United States Patent
Pastor et al.

(10) Patent No.: US 9,840,691 B2
(45) Date of Patent: *Dec. 12, 2017

(54) ONE-WAY SEPARATOR FOR RETAINING AND RECIRCULATING CELLS

(71) Applicant: Bayer Aktiengesellschaft, Leverkusen (DE)

(72) Inventors: Andre Pastor, Solingen (DE); Juri Seletzky, Berkeley, CA (US); Helmut Brod, Cologne (DE); Joerg Kauling, Bergisch Gladbach (DE); Peter Commer, Siegburg (DE)

(73) Assignee: BAYER AKTIENGESELLSCHAFT, Leverkusen (DE)

( * ) Notice: Subject to any disclaimer, the term of this patent is extended or adjusted under 35 U.S.C. 154(b) by 499 days.

This patent is subject to a terminal disclaimer.

(21) Appl. No.: 14/379,324

(22) PCT Filed: Feb. 20, 2013

(86) PCT No.: PCT/EP2013/053393
§ 371 (c)(1),
(2) Date: Aug. 18, 2014

(87) PCT Pub. No.: WO2013/124329
PCT Pub. Date: Aug. 29, 2013

(65) Prior Publication Data
US 2015/0024478 A1    Jan. 22, 2015

(30) Foreign Application Priority Data

Feb. 20, 2012 (EP) .................................... 12001121

(51) Int. Cl.
*C12M 1/12* (2006.01)
*C12M 1/26* (2006.01)
(Continued)

(52) U.S. Cl.
CPC ............ *C12M 33/22* (2013.01); *C12M 23/06* (2013.01); *C12M 23/14* (2013.01); *C12M 23/26* (2013.01);
(Continued)

(58) Field of Classification Search
CPC ...... C12M 23/06; C12M 23/14; C12M 23/26; C12M 23/28; C12M 27/16; C12M 29/04; C12M 33/22

See application file for complete search history.

(56) References Cited

U.S. PATENT DOCUMENTS 4,268,392 A * 5/1981 Hayes .................... E03C 1/264
                                                 210/238
4,783,255 A * 11/1988 Bogusch ............ B01D 21/0051
                                                 210/522
(Continued)

FOREIGN PATENT DOCUMENTS

DE     7215337 U    8/1972
DE     2548950 A1   3/1977
(Continued)

OTHER PUBLICATIONS

English language machine translation of DE10223536 (Dec. 18, 2003), pp. 1-8.*
(Continued)

*Primary Examiner* — William H Beisner
(74) *Attorney, Agent, or Firm* — McBee Moore Woodward & Vanik IP, LLC

(57) ABSTRACT

The invention relates to the use of single- or multilayer plastic web plates in a sloped channel-type solid material separator with a lamella package.

15 Claims, 10 Drawing Sheets

(51) Int. Cl.
  *C12M 1/00* (2006.01)
  *C12M 3/06* (2006.01)
(52) U.S. Cl.
  CPC ............ *C12M 23/28* (2013.01); *C12M 27/16* (2013.01); *C12M 29/04* (2013.01); *C12M 47/02* (2013.01)

(56) References Cited

U.S. PATENT DOCUMENTS

| | | | |
|---|---|---|---|
| 4,814,278 | A | 3/1989 | Hamamoto et al. |
| 5,350,527 | A | 9/1994 | Kitko |
| 5,698,102 | A | 12/1997 | Khudenko |
| 5,817,505 | A | 10/1998 | Thompson et al. |
| 6,959,618 | B1 | 11/2005 | Larsen |

FOREIGN PATENT DOCUMENTS

| | | |
|---|---|---|
| DE | 4401576 A1 | 7/1995 |
| DE | 10223536 A1 | 12/2003 |
| DE | 102010015236 A1 | 10/2011 |
| EP | 0471947 A1 | 2/1992 |
| EP | 0599651 A2 | 6/1994 |
| WO | 94/26384 | 11/1994 |
| WO | 9807828 A1 | 2/1998 |
| WO | 9958222 A1 | 11/1999 |
| WO | 0005337 A1 | 2/2000 |
| WO | 03020919 A2 | 3/2003 |
| WO | 2009139703 A1 | 11/2009 |
| WO | 2009152990 A2 | 12/2009 |
| WO | 2011142670 A1 | 11/2011 |

OTHER PUBLICATIONS

International Search Report received in corresponding PCT/EP2013/053393, dated Apr. 4, 2013.

Henzler, H.J., Chemi-Technik, vol. 1 (1992) No. 3; Cited on p. 2 of the specification.

Binder, H.-J. Sedimentation from single grain and multigrain suspensions in inclined, laminar-flow circular and rectangular pipes, Dissertation Berlin (1980); pp. 1-8.

\* cited by examiner

ONE-WAY SEPARATOR FOR RETAINING AND RECIRCULATING CELLS

CROSS REFERENCE TO RELATED APPLICATIONS

This application is a §371 National Stage Application of PCT/EP2013/053393, filed Feb. 20, 2013, which claims priority to EP 12001121.8, filed Feb. 20, 2012.

BACKGROUND

Field of the Invention

The invention relates to the use of single-layer or multi-layer plastic web plates in an inclined channel solids separator containing a plate stack for retaining solids from a reactor mixture.

Description of Related Art

The culturing of animal and plant cells is of great importance in the production of biologically active substances and pharmaceutically active products. Especially the culturing of cells which is frequently carried out in a free suspension in a growth medium is demanding because the cells, in contrast to microorganisms, are highly sensitive with respect to mechanical shear stress and insufficient nutrient supply.

Animal and plant cell lines are usually cultured in batches. The disadvantage of this is that optimal nourishment of the cells can be achieved only with difficulty because of the constantly changing substrate, product and biomass concentrations. Also, at the end of fermentation, there is accumulation of byproducts, for example constituents of dead cells, which usually need to be removed with great effort in later processing. For the reasons mentioned, but especially when producing unstable products which, for example, can be damaged by proteolytic attacks, use is therefore made of continuously operated bioreactors.

Continuous bioreactors make it possible to achieve high cell densities and an associated high productivity when the following requirements are met:
- sufficient and low-shear supplying of the cells with substrates, especially with dissolved oxygen,
- sufficient removal of the carbon dioxide arising during respiration,
- an effective, low-shear, clog-proof cell-retention system for building up high cell concentrations,
- long-term stability (sterility, hydrodynamics) of the bioreactor and retention system.

In addition to the continuous mode of operation, it is possible to use a bioreactor having an efficient cell-retention system, for example even for the culturing of precultures having especially high cell densities. In this case, the cell-retention system is used discontinuously in repeated-batch mode in order to remove cell culture supernatant virtually free of biomass. Thereafter, the preculture reactor can be refilled with fresh growth medium in order to thus bring the culture to higher cell densities than in the case of simple batchwise operation.

Efficient retention of cells is necessary so that a high cell density (>20 million viable cells per milliliter) can be achieved in a continuously operated bioreactor. In this case, the required degree of retention depends on the growth rate of the cells and the perfusion rate $q/V$ (media throughput $q$ per bioreactor volume $V$).

In the past, different cell-retention systems for continuously operated bioreactors were proposed, which are arranged in most cases outside the bioreactor. The reason for this is the easy accessibility of the cell-retention system for the purposes of maintenance and cleaning.

In order to minimize cell damage, especially owing to insufficient oxygen supply and carbon dioxide removal outside the bioreactor, it is desirable to have cell-retention systems having small working volumes and associated short cell residence times.

In addition to membrane filters, apparatuses which function according to the principle of cross flow filtration with fixed and movable membranes, use is made in the prior art of specific centrifuges and gravity separators.

In the case of cell retention using membrane filters, deposits or contaminations are observed, which can prevent reliable and maintenance-free long-term operation. The deposits can be reduced when there is sufficient rapid flow across the membrane surfaces. This can be achieved in stationary or oscillating operation. An example of a membrane system where there is oscillating flow across it is the Alternating Tangential Flow (ATF) System from Refine Technologies Inc. However, the rapid flow across the membrane surfaces is contrary to the basic prerequisite of low-shear cell culturing.

Low-shear centrifuges for separating off cells in the centrifugal field operate without maintenance only over a few weeks and require replacement of the centrifuge elements. This increases the risk of contamination.

The gravity separators used predominantly in the culturing of cells are settling containers and inclined channel separators. Compared with simple settling containers, the inclined channel separators on large scales have the advantage of a considerably lower volume in relation to the separation surface area. One publication (Henzler, H.-J., Chemie-Technik, 1, 1992, 3) describes the cell retention in inclined channel separators which can be operated in countercurrent flow, cross flow and cocurrent flow. The channel cross section through which flow passes can be provided with plates or tubes. WO1994026384 A1 claims the use of inclined channel separators for retaining cells in countercurrent flow separators. WO2003020919 A2 describes, inter alia, countercurrent flow and cross flow separators, and also combinations with various preseparators (e.g., hydrocyclones), for the retention of cells. These known inclined channel separators are made from stainless steel, and the elements thereof are cut, smoothed with effort, mirror polished and welded together.

The inclined channel separators are connected to the bioreactor via an external circuit. For this purpose, hose lines and pumps are required.

To reduce metabolic activity and the adherence of cells in a gravity separator, cooling of the cell culture broth on its way to the gravity separator is proposed. Reduced metabolic activity at low temperature is certainly advantageous in the case of extended residence of cells outside the bioreactor.

WO2009152990 (A2) describes a cell-retention system for retaining and recirculating cells in a vessel through which flow passes, comprising a multiplicity of channels arranged next to one another, with the channels forming an upright hollow cylinder and being tilted at an angle β between 10° and 60° with respect to the longitudinal axis of the hollow cylinder. The vessel through which flow passes can be a bioreactor or a bioreactor-connected vessel for cell retention and recirculation. The channels are opened at the lower end. At the upper end, they lead to a common ring space having at least one line via which a harvest stream can be conveyed from the vessel. The separation of cells and cell culture solution takes place in the channels. As a result of the continuous removal of the harvest stream from the bioreactor, cell culture solution and cells are sucked into the channels. The cells sediment within the tilted channels and slide, as in classic inclined channel separators, in countercurrent flow with respect to the inflowing harvest stream out of the channels again and thus remain in the vessel. The cell culture solution separated from the cells is conveyed through the channels into the ring space above the channels and ultimately out of the vessel.

In highly regulated pharmaceutical production, providing cleaned and sterilized bioreactors and bioreactor elements such as, for example, cell-retention systems is time-consuming, technically complicated and personnel-intensive to a great extent. To safely avoid cross contamination during a product change in a multipurpose unit or between two product lots, very complex cleaning validation is required besides the cleaning, which validation possibly needs to be repeated in the case of a process adaption. For the cleaning and sterilization of a conventional batch, fed batch or perfusion fermenter made of stainless steel, use is generally made of clean-in-place (CIP) technology in combination with steam-in-place (SIP) technology in so-called permanent-fixture units. To ensure sufficient long-term sterility in the case of continuous process control, use is also made of autoclave technology, which, however, requires inconvenient transport of the reactors or reactor elements to the autoclave and is only applicable on comparatively small reactor scales. The risk of contamination is especially critical in the case of use of aging expendable parts, for example sealed agitator shafts, improper sterilization or equipment transport, putting into operation of or connection of connecting lines after autoclaving, and regular sampling.

In the case of CIP/SIP units used in batch or fed-batch mode, the reactor downtime caused by the preparation procedures can significantly affect reactor availability, especially in the case of frequent product change because of the short periods of use.

Concepts for disposable reactors are receiving increasing interest in the market to meet the demand for rapid and flexible production unit reloading while ensuring maximum cleanliness and sterility.

SUMMARY

Proceeding from the prior art, it is an object of the present invention to provide an efficient method for retaining and recirculating animal, especially human, and plant cells in a continuously or batchwise operated process, which method takes into account the sensitivity of the cells with respect to mechanical shear stress and sufficient nutrient supply to the cells, which method is scalable up to very large scales, which method meets the maintenance, cleaning and sterilization requirements of the pharmaceutical industry, the use of which method lowers complexity and the risk of error, and which method allows, with minimal use of resources, economically and environmentally optimal use (production and disposal) as disposable systems.

The aforementioned object was achieved by the use of single-layer or multilayer plastic web plates in an inclined channel solids separator containing a plate stack for retaining solids from a reactor mixture.

For the retention of cells in particular from a bioreactor mixture, the inclined channel solids separator according to the invention comprises the following elements:

- an upper region of the solids separator having one or more feed-throughs/fittings (80) for removing a harvest stream (70) separated from the cells (=harvest) from a harvest stream collection region (56), connected to
- a separation region formed by a plate stack (1) composed of single-layer or multilayer plastic web plates, which stack is tilted during operation at an angle (10) of from 30° to 80° with respect to the horizontal, connected to
- a lower segment of the solids separator having one or more feed-throughs or fittings (84) for flow distribution of the reactor mixture (74), above
- a solids collection region (57) which is downwardly tapered, especially in a conical or pyramidical manner, for collecting the cells by means of gravity.

Preferably, the solids collection region (57) which is downwardly tapered, especially in a conical or pyramidical manner, has an angle (58, 59) of from 10° to 60° with respect to the vertical. The angles 58 and 59 can be selected separately.

To allow recirculation, the solids collection region (57) has one or more feed-throughs (89) or possibly fittings (88) for removing the cells. An example of fittings is a central suction port.

The single-layer or multilayer plastic web plates form channels and the plate stack 1 preferably consists of a multiplicity of channels arranged next to one another.

The channels are opened at the lower end and at the upper end. At the lower end, the channels lead to the common solids collection region 57 which is downwardly tapered in a conical manner. At the upper end, they lead to a common harvest stream collection region 56, which has at least one feed-through 80 through which the harvest stream can be conveyed from the vessel.

In the channels of the inclined channel solids separator according to the invention, cells and cell culture solution are separated. As a result of the continuous removal of the harvest stream from the bioreactor, cell culture solution and cells are sucked into the channels. The cells sediment within the tilted channels and slide, as in classic inclined channel separators, in countercurrent flow with respect to the inflowing harvest stream out of the channels again and are collected in the conically tapered solids collection region 57. Usually, the solids collection region 57 has one or more feed-throughs/fittings 88/89, connected to the bioreactor for sucking off the collected cells and recirculation into the bioreactor.

The channels of the plate stack 1 can have an angular, elliptical, round or semicircular cross section (FIG. 4).

The dimensioning of the channels (number, diameter, length) depends in each case on the nature of the cells to be retained, the size of the bioreactor and the throughput.

The channel width d is preferably d≥3 mm in order to prevent clogging of the channels. In a preferred embodiment, channels having a channel width of from 3 mm to 100 mm, preferably from 4 mm to 20 mm, particularly preferably from 3-7 mm, are used in order, firstly, to safely avoid clogging states and, secondly, to minimize the space-time yield-reducing volume ratio between separator space and bioreactor space.

The required separation surface area $A_{erf}$ arises from the sedimentation rate ws, the perfusion rate q/V (media throughput q per bioreactor volume V) and the bioreactor volume as per eq. 1. A coefficient η takes into account the reduction in performance of inclined channel separators with respect to vertical separators (eq. 2).

The theoretical separation surface area $A_{th}$ in the case of rectangular and cylindrical cross sections can be approximately determined from eqs. 3 and 4 according to approaches published in the literature (H.-J. Binder, Sedimentation aus Ein-und Mehrkornsuspensionen in schräg stehenden, laminar durchströmten Kreis-und Rechteckrohren [Sedimentation from single grain and multigrain suspensions in inclined, laminar-flow circular and rectangular pipes], Dissertation Berlin, 1980):

$$A_{erf} = \frac{\text{Perfusion rate} \cdot V}{ws} \quad \text{(Eq. 1)}$$

$$A_{th} = \frac{A_{erf}}{\eta} \quad \text{(Eq. 2)}$$

$$\text{Rectangle: } A_{th} \approx Z \cdot \sin(\beta) \cdot d \cdot L \quad \text{(Eq. 3)}$$

$$\text{Cylinder: } A_{th} \approx \frac{3 \cdot \pi}{16} \cdot Z \cdot \sin(\beta) \cdot d \cdot L \quad \text{(Eq. 4)}$$

Here, Z is the number of channels, β is the angle by which the channels are tilted with respect to the direction of gravity, d is the inner diameter and L is the length of the channels. π is the number pi (π=3.14159 . . . ).

Dimensioning of channel length requires observance of laminar flow conditions (Reynolds number Re<2300) to be taken into account.

In this connection, the dynamic pressure at the harvest stream removal site (=feed-throughs/fittings 80) should be at least 5 to 10 times lower than the pressure drop in the channels in order to rule out the efficiency-reducing phenomenon of maldistribution. Sufficient pressure drops can be considered to be technically realizable in the case of channel lengths from 0.1 m, whereas preferably channel lengths of from 0.2 m to 5 m, particularly preferably channel lengths of from 0.4 m to 2 m, are realized.

Owing to the reduced pressure drops, short channel lengths L can lead to distribution problems, and this, especially when removing the harvest stream from the upper harvest stream collection region 56, may require a distribution device for reducing the rates of removal. Optionally, the feed-throughs/fittings 80 therefore have flow inverters 81 for homogenized removal of the harvest stream 70 separated from the cells (=harvest) from a harvest stream collection region 56.

Usually, the inclined channel solids separator according to the invention can comprise from 1 to $10^6$ channels, preferably from 10 to 100 000, particularly preferably from 10 to 10 000. The channels are, where necessary, distributed across one or more web plates in a plate stack 1 for space requirement optimization. Preferably, the plate stack 1 comprises from 1 to 400 web plates, particularly preferably from 1 to 50 web plates, depending on the scale.

The width to height ratio of the plate stack 1 consisting of single-layer or multilayer web plates including the supporting plate can be adjusted. Plate stacks 1 having a square, cylindrical, rectangular or elliptical cross section having a height to width ratio H/D of 0.005≤H/D≤1.5, preferably 0.02≤H/D≤1.2, particularly preferably 0.1≤H/D≤1.0, are preferably used.

Preferably, the separation region comprises multiple plastic web plates which are stacked on top of one another and which form a base body.

Alternatively, the plate stack 1 can be formed from a profiled plate 340 or 320 (see FIG. 4). A profiled plate preferably has a smooth side and a side having a succession of struts and grooves at constant intervals. Channels are formed upon stacking of the plate in one or more layers, for example on a supporting plate 30. In this case, the grooves on the open side are in each case closed by the smooth side of an adjacent layer or by the wall of the stator. It is also possible to extrude a plate stack or substack in a single-layer or multilayer manner and to join them to form a plate stack 1.

The web plates are preferably joined by means of adhesive bonding or welding. The plate stack should primarily be spatially fixed as a result of joining. Another aim is to minimize the so-called dead zones (spaces not used for separation around the exterior surfaces of the web plates). However, in this case, complete avoidance of said dead zones is not absolutely necessary. Suitable adhesives are the adhesive components known to a person skilled in the art and tailored to the material and surface properties of the channels. More particularly, preference is given to using an adhesive available on the market in the required FDA quality classes. For welding, thermal joining techniques such as heat, laser and ultrasound can be used. A particularly preferred joining technique is laser welding, which can also be used especially in combination with cutting the plate stack to size in a device suitable for this purpose. Welding technology has the advantage that the number of plastics introduced into the pharmaceutical process is not increased by this joining technology.

The geometry of the channels is defined by the ratio of the strut height hs to the channel width d. Technically realizable hs/d ratios are within the range of 0.01≤hs/d≤5 depending on characteristics (malleability, elasticity, capacity for deep drawing). It should be noted here that the two dimensions hs and d should both be greater than or equal to 3 mm, or preferably greater than or equal to 5 mm. Preferred hs/d ratios are from 0.5 to 5. The strut widths bs are determined by the mechanical stability of the film material. The strut widths bs should be minimized to allow high separation surface areas per separator volume. At the same time, they should not be selected too low in order to be able to allow a force-fit connection with the lower layer without a change in shape. In the case of extruded plate stacks 1, or in the case of plate stacks constructed from extruded plate substacks or web plates, it is possible to realize very high rigidity with small strut widths without a huge loss of separation surface area, and so this form of production is preferred.

The profiled plate can be made by shaping directly during plate production or by (e.g., adhesive) joining of an embossed, hot or cold formed plate to a smooth plate. The material properties of the embossed and smooth plate can be optimally adjusted with respect to their different functionality (good sliding properties and shape stability for the embossed plate, good sealing properties for the smooth plate), i.e., by selecting a suitable material known to a person skilled in the art and having appropriate surface quality.

Commercially available, cost-effective, and pharmaceutical process-suited plastic web plates composed of, for example, polycarbonate in the form of plate substacks are usually cut or produced to the appropriate length and attached to one another to produce the plate stack 1.

These web plates are extruded as a continuous product for cutting, having finished channel geometry (sedimentation surface area) and ready-made surface quality. Cutting to size, more particularly cutting to the required length, is usually achieved by sawing off on, for example, a circular saw. Usually, the longitudinal struts serve, firstly, as the housing of the separator and, secondly, to stabilize the flow channels, and the transverse struts serve, firstly, as the housing of the separator and form, secondly, the separation surface area.

The plate stack constructed from plastic web plates is realized either as a straight cuboid (FIG. 3), where the plane of the channel openings is at a right angle with respect to the supporting surface of the plate stack 1, or as a leaning cuboid (FIG. 2), where the channel openings in the fitted state lie on a horizontal plane. The latter solution is preferred in order to prevent a sedimentation-induced concentration gradient toward the lower channel openings. The channels receive homogenized flow of the reactor mixture, optionally with the aid of horizontal distributors 85.

DETAILED DESCRIPTION OF A PREFERRED EMBODIMENT

Figure 1:
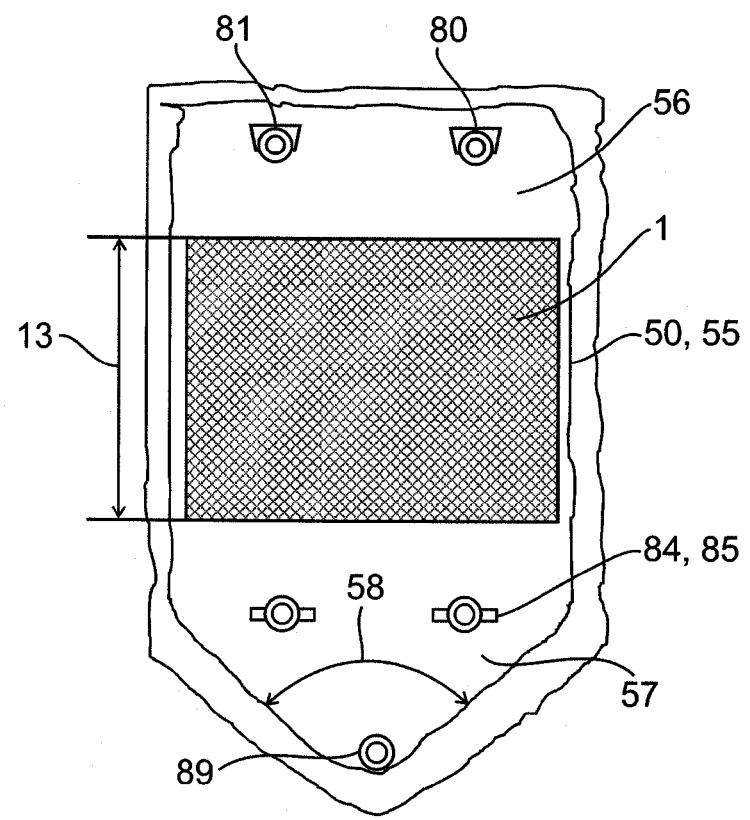
FIGS. 1-16 represents embodiments described herein.

In a first embodiment (FIGS. 1 to 13), the elements of the disposable inclined channel solids separator according to the invention are fitted into a gamma-sterilizable plastic bag through which flow can pass. The plate stack 1 composed of single-layer or multilayer plastic web plates is introduced in the upper segment of the central region of the plastic bag. The plastic bag also delimits the harvest stream collection region 56 and the conically tapered solids collection region, with the solids collection region 57 preferably having an angle 58, 59 of from 10° to 60° with respect to the vertical. In the lower segment of the central region of the plastic bag, feed-throughs or fittings 84 exhibit a horizontal distributor 85 for uniform horizontal flow distribution of the cell culture solution (=feed) 74 via an infeed surface area 510.

In this embodiment, the aforementioned object is achieved by a disposable inclined channel solids separator for retaining and recirculating cells from a bioreactor mixture, comprising a gamma-sterilizable plastic bag through which flow can pass having the following fittings:

in the upper region of the plastic bag, one or more feed-throughs/fittings 80 for removing a harvest stream 70 separated from the cells (=harvest) from a harvest stream collection region 56, in the upper segment of a central region of the plastic bag, a separation region formed by a plate stack 1 composed of single-layer or multilayer plastic web plates, which stack is tilted during operation at an angle ($10=\beta$) of from 30° to 80° with respect to the horizontal, in the lower segment of the central region of the plastic bag, one or more feed-throughs or fittings 84 for flow distribution of the reactor mixture 74, optionally having horizontal distributors 85 for uniform horizontal flow distribution of the cell culture solution (=feed) 74 via an infeed surface area 510, in the lower region of the plastic bag, a solids collection region 57 which is downwardly tapered, especially in a conical or pyramidical manner, for collecting the cells by means of gravity. Usually, the solids collection region 57 has one or more feed-throughs 89 or fittings 88 for removing the cells.

The upper region of the plastic bag can also be upwardly tapered.

The plastic bag is usually realized from a single-layer or multilayer transparent polymer material, which allows the interior of the device to be viewed during operation. In the case of customary low film thicknesses of s<<1 mm, the polymer material permits apparatuses having a comparatively small mass fraction. It is cost-effective to acquire and to process, and this is very highly suited to the construction of disposable systems. Disposal of used separators and use of a new disposable separator are thus more economical than cleaning used separation devices, especially since expensive cleaning with water for injections (WFI) and time-consuming cleaning validation is not applicable when using disposable separators. The separator according to the invention is preferably sterile-packed.

Particularly suitable materials for the plastic bag are the materials and material combinations used in patent specification U.S. Pat. No. 6,186,932 B1, columns 2 and 3, for the transport bags (sachets) mentioned therein. The wall strengths cited therein can also be transferred to the separation device according to the invention.

In a preferred embodiment, the walls of the plastic bag consist of a film composite material known to a person skilled in the art and consisting of two or more layers (laminate or coextrudate) in order to improve the properties of the plastic bag with respect to unfolding behavior, stretching behavior, gas diffusion, stability, process compatibility (minimal adsorption of products and cells) and weldability.

Dimensioning of channel length requires observance of laminar flow conditions (Reynolds number Re<2300) to be taken into account. The channel length L is guided by the length of the available bag interior measurement (=length of the bag LK). The bag length LK to be realized is guided by the fill levels to be realized in the plastic bag and by the hydrostatic pressures to be realized in the plastic bag. Excessively high hydrostatic pressures can, if necessary, be transmitted to appropriately dimensioned, non-product-contacted and therefore reusable enclosures.

The channel lengths L are usually from 30% to 95%, particularly preferably from 60% to 90%, of the length LK of the plastic bag.

The solids separator according to the invention containing a plastic bag composed of polymer films can, for example, be produced according to the method described in U.S. Pat. No. 6,186,932 B1, it being necessary to adjust the welding seams. Exemplary embodiments for producing preferred embodiments of the separation device according to the invention are described further below.

Feed-throughs are usually produced from the same material as that of the product-contacted film in order to allow, with said film, welding which is faultless in terms of sterility and strength. Preferred product-contacted film material is polyethylene of various degrees of crosslinking which are known to a person skilled in the art. Depending on the application and process requirement, the outer jacket films used are various materials known to a person skilled in the art having an increased melting point, with respect to the inner film, for the use of thermal welding methods and/or better strength and/or diffusion properties.

The web plates are usually bound to a supporting plate 30, which offers a foothold and can be joined to the plastic bag by adhesion or welding for exact positioning.

In 3D bags (bags welded together from 4 film webs), it is favorably possible to use plate stacks 1 having a square, cylindrical, rectangular or elliptical cross section having a height-to-width ratio H/D of $0.3<H/D<1.5$, preferably $0.6<H/D<1.2$, particularly preferably $0.9<H/D<1.0$.

Suitable for more simple and more inexpensive 2D bags (bags welded together from two film webs) are planar plate stacks having a rectangular cross section, H/D ratios of $0.005<H/D<1$, preferably $0.02<H/D<0.6$, particularly preferably $0.1<H/D<0.4$. Depending on the height of the plate stack, a certain distance can be left between the plate stack and the start of the tapering(s) for the manufacture of a 2D bag.

For the production of the separator, the feed-throughs and further fittings are also prepared and, if appropriate, fitted in a plastic film at the appropriate sites.

Figure 5:
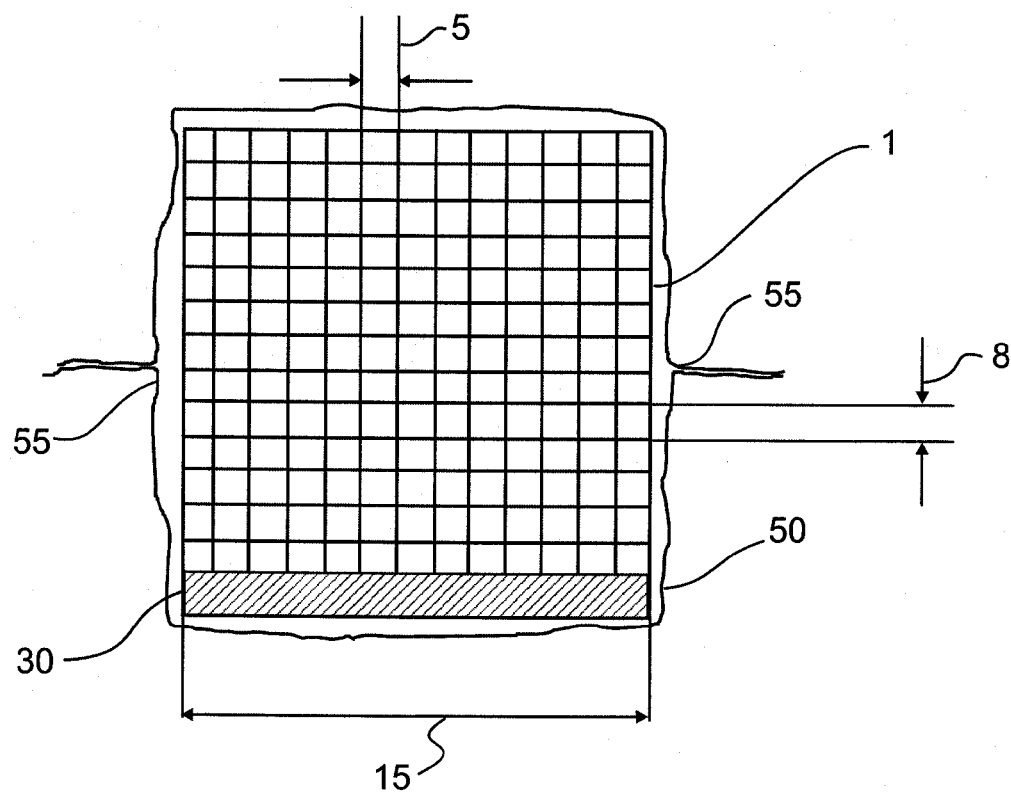

Subsequently, a plastic bag 50 is welded together from the plastic film enclosing the plate stack 1 to give a plastic bag 50 with a welding seam 55 (FIG. 5).

The plate stack 1 including supporting plate is then usually pressed in against the inner surface of the plastic bag 50 in order to prevent the penetration of cells between plastic bag 50 and plate stack 1 and thus fouling.

Figure 6:
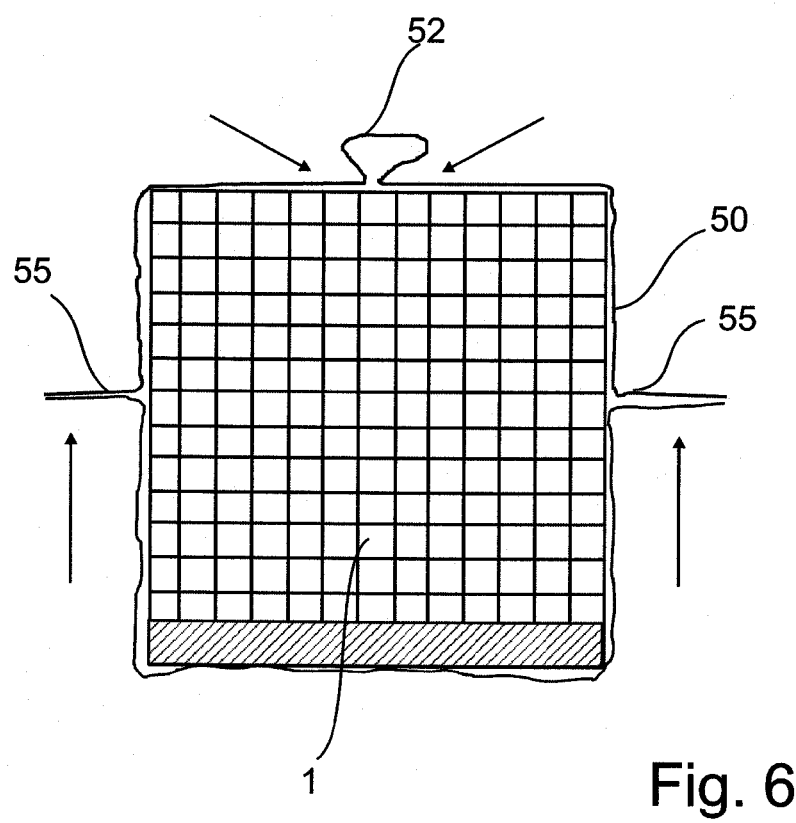

In a first embodiment of the method of production, the plastic bag 50 is tightened onto the plate stack 1 (FIG. 5) and the fold 52 formed is pressed flat and secured using one or more fastening straps 60 (FIG. 6). A plastic film which is tightly wrapped around bag and plate stack is also suitable as a fastening strap. Favorable tightening properties are found in, for example, household films or flexible, thin silicone films. Welding of the plate stack 1 to the bag wall may also be appropriate for establishing a tight connection between bag and plate stack.

For operation, the device according to the invention is oriented at an angle 10=β with respect to the horizontal. The angle β is guided by the settling and sliding behavior of the cells/solids and is 30°≤β≤80° with respect to the horizontal during operation. In a preferred embodiment, the angle β is from 35° to 75°, particularly preferably from 45° to 60°, with respect to the horizontal.

Figure 11:
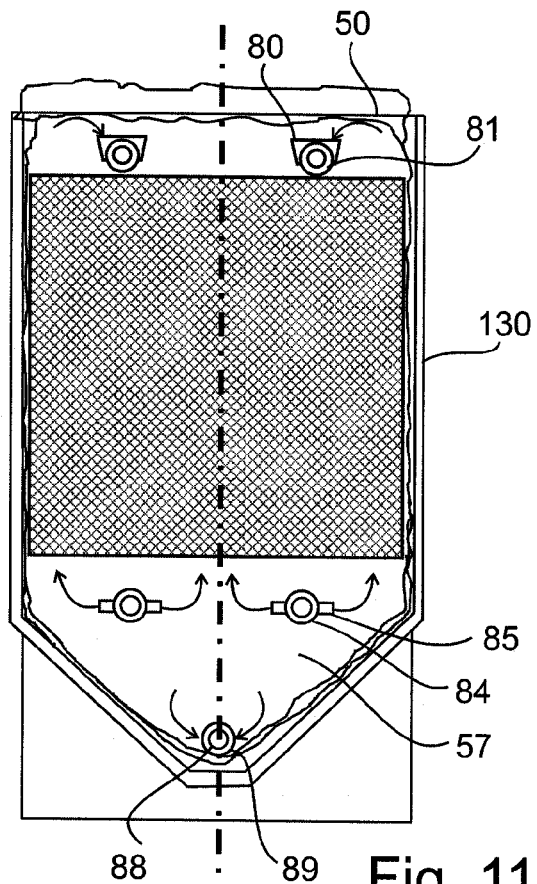
Figure 12:
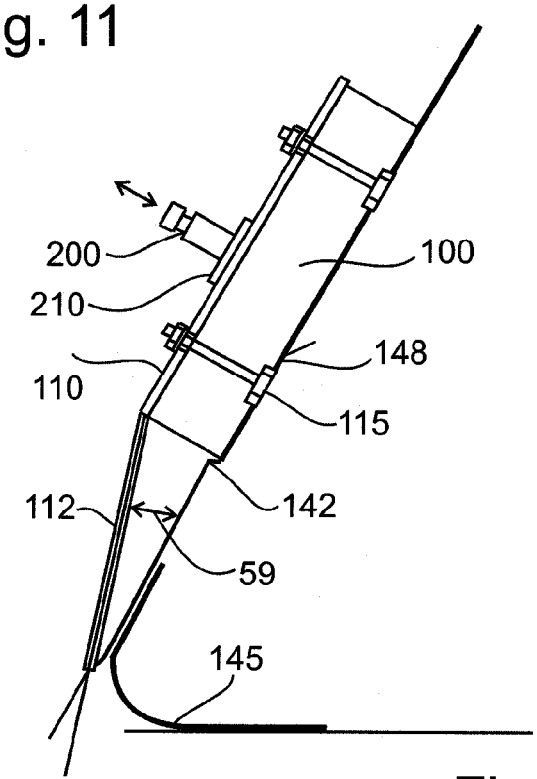
Figure 13:
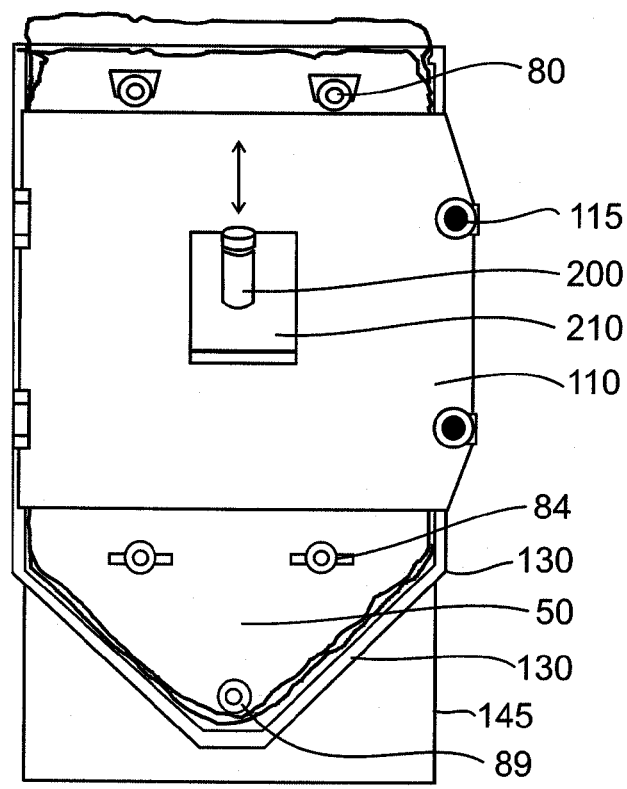

To ensure the angle β during operation, the solids separator according to the invention is secured to a frame 140 for operation (FIGS. 11 to 13).

The frame 140 usually comprises a frame foot 145 and a support 148 having a predefined angle 10 (=β) with respect to the footprint. On the support 148, the plate stack 1 including supporting plate 30 is held at a predefined height by means of a projection 142 and/or lid 110 and also fastening elements 115, so that both the harvest stream collection region 56 (above) and the solids collection region 57 can rest on the support with minimal creases during operation. This reduces dead spaces and corresponding fouling.

In a preferred embodiment, the frame 140 has a housing 100 and a lid 110 for accommodating the plate stack 1.

In this case, the tightening process can also take place during fitting of the solids separator according to the invention onto the frame 140 and, more particularly, in the housing 100 and lid 110 (FIGS. 6 and 7), possibly also without wrapping with a fastening strap 60. Here, the plastic bag 50 is kept in position on the supporting plate 30 and on the plate stack 1 by means of the housing 100 and the fold 52 is pressed onto the plate stack 1 by means of the lid 110. Preferably, the lid 110 is fastened on the housing 130 on one side by means of, for example, hinges and on the other side by means of one or more lockable fastening elements 115. This makes it simpler to manipulate the frame 140 for starting up the solids separator according to the invention.

In a preferred embodiment, the lid 110 has an extension 112 and/or a framework 130 which keeps the conically tapered solids collection region 57 in shape, more particularly the angle 59 constant, and prevents the expansion thereof in the filled state during operation. Such a shape-matching container is, inter alia, advantageous for the operation of the system at relatively large hydrostatic forces, as are to be expected when connecting to large bioreactors.

The inclined channel solids separator according to the invention is preferably realized as a disposable article in order to avoid cleaning problems.

Storage of the inclined channel solids separators according to the invention saves space, since they can be stacked on top of one another without any problems and are set up at the appropriate angle only during start-up. They can then be easily connected and operated outside a bioreactor.

In a further embodiment (FIGS. 14 and 15), the upper region of the inclined channel solids separator according to the invention is a collector, which, for example, is made from an article having a hose connection by cutting a plastic solid rod composed especially of polycarbonate such as Makrolon® on a turning machine. A further method, which is primarily suitable in the case of high article quantities, is an injection molding process. The collector exhibits feed-throughs (80), at least one feed-through for removing a harvest stream (70) separated from the cells (=harvest) connected to the harvest stream collection region 56. The harvest stream collection region 56 is formed by a recess in the collector, which recess opens into the feed-through 80 for removing a harvest stream (70) separated from the cells. The cross section of said recess is usually round or square. Preferably, the cross section is adapted to the size of the opening of the upper plug plate and hereby to the edge dimensions of the web-plate base body. The height of the recess is adjusted with respect to minimization of the dead volume and optimization of flow control. It is usually from 1 to 5 mm. Said recess can also be funnel-shaped.

In this embodiment, the upper and the lower end of the web-plate base body are introduced into and adhesively bonded in so-called plug plates. The plug plates are also usually made by cutting on a turning and milling machine or in an injection molding process. They are preferably composed of the material of the collector. They exhibit a square opening, preferably at a predefined angle, for plugging of the lower and upper ends of the web-plate base body. They are usually round.

Preferably, a funnel forms the lower segment and the solids collection region (57), which has one or more feed-throughs 89 for removing the solids. The funnel is usually made with a lower hose connection by cutting on a turning machine or in an injection molding process. It is preferably composed of the material of the plug plates. The upper region of the funnel exhibits one or more feed-throughs or fittings 84 for uniform flow distribution of the cell culture solution (=feed) 74 via an infeed surface area 510. The optional horizontal distributor can be formed by two or more geometrically distributed holes, usually two opposing holes, in which lateral connections are glued in place. The funnel is adhesively bonded to the lower plug plate.

Preferably, the solids collection region (57) which is downwardly tapered, especially in a conical or pyramidical manner, has an angle (58, 59) of from 10° to 60° with respect to the vertical. The angles 58 and 59 can be selected separately.

The collector, the plug plates and the funnel are usually resistant to bending for the mechanical stability of the inclined channel solids separator.

Preferably, the web-plate base body is stabilized by means of a stiffening bracket. The stiffening bracket is attached by adhesive bonding to the web-plate base body and to the upper and lower plug plate and ensures sufficient mechanical stability of the inclined channel solids separator.

Compared to the stainless-steel inclined channel separators from the prior art, the complicated manufacture of the base body (cutting, numerous welding steps, and electropolishing to a very smooth finish) is not applicable in the case of the inclined channel solids separators according to the invention (=plastic-plate separators). Complicated welding is replaced by simple adhesive bonding. Producing the inclined channel separator according to the invention requires no screwing and no sealing. Altogether, considerable advantages in terms of time and material costs are achieved in the production of the plastic-plate separator compared to the stainless-steel inclined channel separator.

Said inclined channel solids separator according to the invention is usually produced as follows:
a. cutting to size, more particularly sawing, of the web-plate base body,
b. deburring and cleaning of the web-plate base body,
c. production of the following components:
   1) Funnel
   2) Two plug plates
   3) Collector
   4) Preferably a stiffening bracket
d. bilateral insertion of the web-plate base body into the plug plates, and adhesive bonding, preferably with a UV-curing adhesive such as, for example, Loctite 3211,
e. adhesive bonding of the upper plug plate to the collector,
f. adhesive bonding of the lower plug plate to the funnel,
g. attachment and adhesive bonding of the stiffening bracket.

For operation, the inclined channel solids separator is usually secured on a console.

Owing to the plastic construction and the resulting reduced weight, a reusable console made of stainless steel suffices, depending on size, for installation. For an inclined channel separator of customary size (separator surface area of 0.15 m$^2$), a total weight including console of approx. 4 kg was achieved (compare with stainless steel of identical size, approximately 40 kg). This makes the disposable inclined channel separator according to the invention easily transportable with no need for a mobile transport frame.

Figure 16:
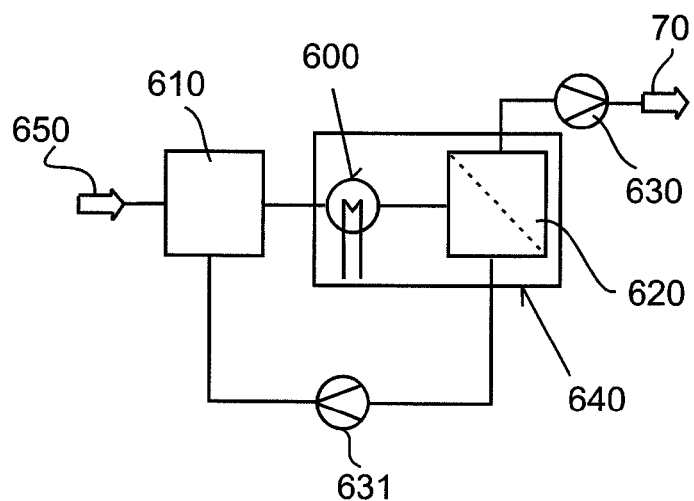

Usually, the inclined channel solids separators according to the invention are externally coupled by means of hose lines to a bioreactor, for example to a disposable bioreactor as described in US 2009-0180933. Ensuring the separator according to the invention is supplied is achieved by at least two pumps, preferably low-shear peristaltic pumps (FIG. 16). The pumps allow the removal of the cell culture solution from the bioreactor space, the feeding thereof after cooling across a heat exchanger to the separator device, the removal of the harvest stream from the separator device and the return transport of the solids stream (=return 70) to the bioreactor. The required separation surface areas are guided by the sedimentation properties of the cells and by the perfusion rates and cell concentrations striven for. Preferred perfusion rates are within the range of from 0.1 to 40 1/day, particularly preferably from 0.5 to 20 1/day. Preferred separation surface areas per bioreactor volume are within the range of from 0.1 to 100 m$^2$/m$^3$, particularly preferably from 2 to 20 m$^2$/m$^3$, depending on the sedimentation properties of the cells (dependent on the concentration, size and agglomeration tendency of the cells).

The methods described allow simple and cost-effective production of the inclined channel solids separator according to the invention for retaining and recirculating cells. Owing to the plate-stack configuration variable within wide limits, the geometry of the subsequent device can be easily and precisely defined and, in contrast to stainless-steel systems, can also be provided for very large bioreactors. The methods described allow in particular cost-effective production of disposable elements, the use of which makes it possible to reduce to a minimum the effort required for providing a retention system cleaned according to pharmaceutical guidelines.

Connection to the fermenters is carried out by means of sterile couplers, attached at the end of the hose lines, from various manufacturers (Pall, Sartorius, Coulder) inside or outside laminar flow cabinets, but preferably by hose welding. The hose lines attached to the solids separators according to the invention are therefore preferably—at least in part—provided with a hose welding-suited hose element. In addition, for conveying the suspension, the hose lines usually contain at least two specific hose elements highly resistant to mechanical stress (e.g., composed of Verderprene elastomer hose from Verder) which can be inserted noninvasively into peristaltic pumps without endangering the sterility of the separators. Connection, operation and maintenance are problem-free. Realization of the device according to the invention or parts of the device according to the invention as a disposable element eliminates cleaning problems.

To improve the sliding behavior of the cells in the channels of the plate stack and on the inner walls of the conically tapered solids collection region, the device can be made to vibrate using suitable means, for example pneumatic or electric vibrators.

Direct use of the plate stack 1 in aerobic bioreactors is conceivable in principle if the gas bubbles necessary for gas application can be kept away from the entrance openings.

Preferably, the separator according to the invention is, however, intended for use outside a bioreactor.

The present invention further provides a bioreactor unit consisting of a bioreactor and one of the described cell separation devices according to the invention. Preferably, the bioreactor is a disposable reactor, more particularly a reactor described as in US 2009-0180933.

The bioreactor unit is, for example, a perfusion reactor which can be operated in a manner which is known. Growth medium is continuously fed to the bioreactor, and cell culture supernatant low in cells is continuously purged. The perfusion reactor can be operated at high perfusion rates q/V (media throughput q per bioreactor volume V) when this is useful from a biological point of view and a sufficient separation surface area is provided. In this case, flow continuously passes through the separator.

The perfusion reactor can also be operated in such a way that a culture is initially allowed to achieve high growth in a batchwise manner. When the medium has been greatly consumed to such an extent that appreciable build-up of biomass is no longer possible, culture supernatant virtually free of biomass is removed via the external cell separator. The space gained in the bioreactor can then be used in order to feed fresh growth medium, allowing further growth and thus higher total biomass productivity (repeated-batch mode). In this case, flow passes through the cell separator in a batchwise manner. This method is suitable for, for example, precultures with which very large bioreactors are to be inoculated, since it can increase the productivity of existing preculture reactors.

For operation on bioreactors, continuous flow of the inclined channel solids separator according to the invention is preferred.

The bioreactor or perfusion reactor can be used for culturing cells which grow in vitro and in free suspension or on microcarriers. The preferred cells include protozoa and also adhesive and nonadhesive eukaryote cells of human (nerve, blood or tissue cells, and also stem cells of embryonic or adult origin), animal or plant origin which are capable as a result of, for example, a genetic modification of producing specific active pharmaceutical ingredients such as viruses, proteins, enzymes, antibodies, neurones, tissue cells or diagnostic structures. Particularly preferably, cells suitable for high-performance pharmaceutical production are used, for example ciliates, insect cells, baby hamster kidney (BHK) cells, Chinese hamster ovary (CHO) cells, HKB cells (resulting from the fusion of the human HEK 293 cell line with the human Burkitt's lymphoma cell line 2B8), hybridoma cells and also stem cells.

In an alternative embodiment of the unit, one of the described cell separators according to the invention in batchwise operation is, upon completion of fermentation before cell removal, connected to a further bioreactor or a harvest tank with the goal of reducing the cell mass to be applied to the filters and thus the required filter surface areas.

The method for retaining and recirculating solids, more particularly cells, is carried out in the inclined channel solids separator through which flow passes, with solids-containing medium being fed in a continuous or batchwise manner to the inclined channel solids separator and solids-free medium being purged, with a flow rate permitting the preservation of laminar flow states as per Re<2300 prevailing, avoiding efficiency-reducing resuspension of the separated cells against the gravity field.

The Reynolds number Re can be calculated according to eq. 7 from the flow rate w averaged across the cross section, the kinematic viscosity v of the flowing medium and the inner diameter d of a channel:

$$Re = (w \cdot d/v) \quad \text{(Eq. 7)}$$

In inclined channels, the flow rate is lower on the channel inner walls than in the channel centers. The cells sediment in the channels and counterslide on the underside of the channels against the flow direction to the lower channel ends. The cell culture solution relieved of the cells is released by the channels into a harvest stream collection region 56, which is arranged above the channels, and eventually conveyed from the vessel.

The method according to the invention may preferably be carried out outside a bioreactor. To this end, the cell culture solution containing cells is conveyed from the bioreactor into the cell separator according to the invention. Preferably, the cells are cooled in an external vessel before entering the separator in order to slow down metabolism and thus counteract productivity-reducing undernourishment of the cells. In cooled suspension, supplying oxygen to the sedimenting cells is not required. In most cases, cooling of the cell culture solution down to the ambient temperature of the separators is completely sufficient, and so, besides the desired metabolic effect, convection currents are safely avoided. To monitor sufficient nourishment of the cells, the separator can be provided with at least one disposable sensor, for example for measuring the oxygen concentration and/or pH. Accommodation of the sensors is possible both in the walls and the connecting line to the bioreactor or the harvest vessels.

The method allows effective retention and recirculation of cells in a sterile plastic bag through which flow continuously passes. During retention and recirculation, the cells are acted on by moderate shear forces only, which are usually well tolerated by the cells. The cells are kept in the separation device at fermentation temperature or a reduced temperature level and the supply of nutrients is provided.

Exemplary embodiments of the invention will now be more particularly elucidated with reference to drawings without restricting the invention thereto.

FIG. 1. Diagram showing the disposable solids separators according to the invention containing plate stack.

Figure 2:
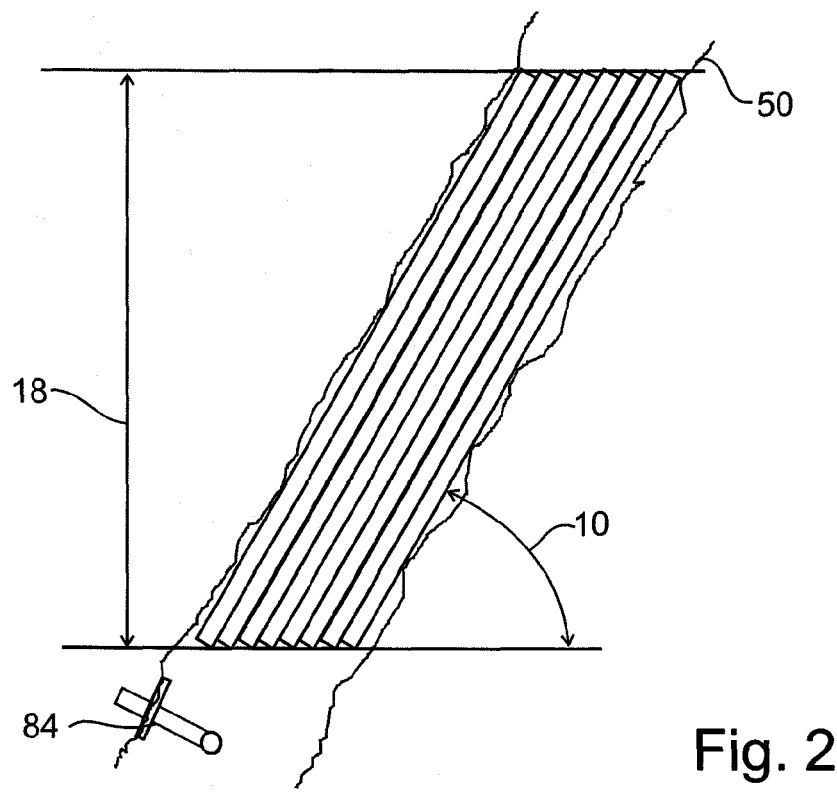

FIG. 2 Diagram showing a plate stack 1 (longitudinal section)

Figure 3:
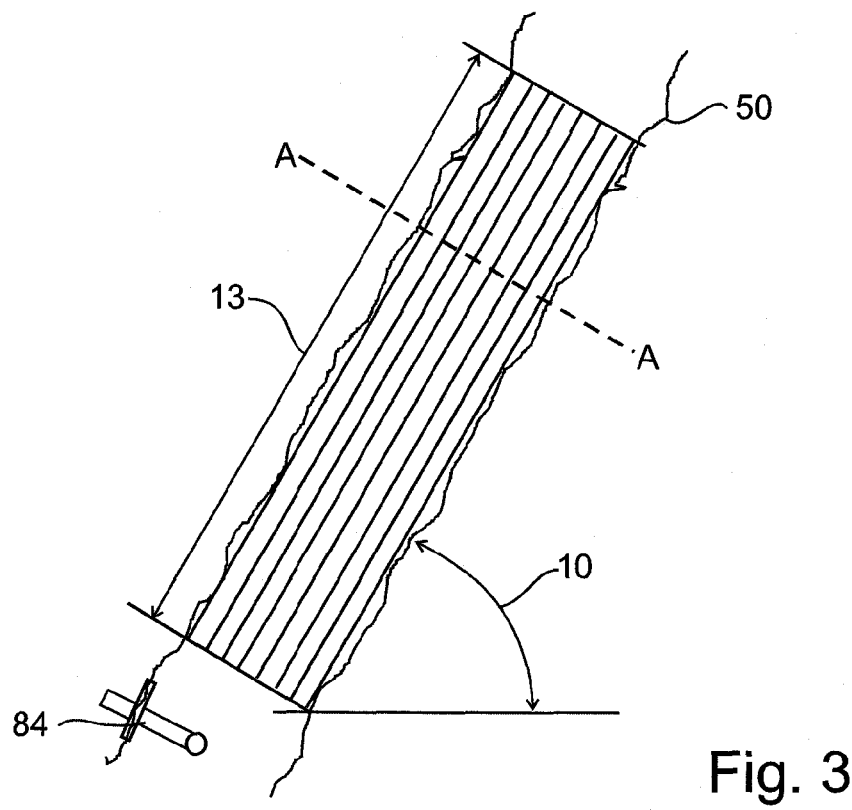

FIG. 3 Diagram showing a plate stack 1 (longitudinal section)

Figure 4:
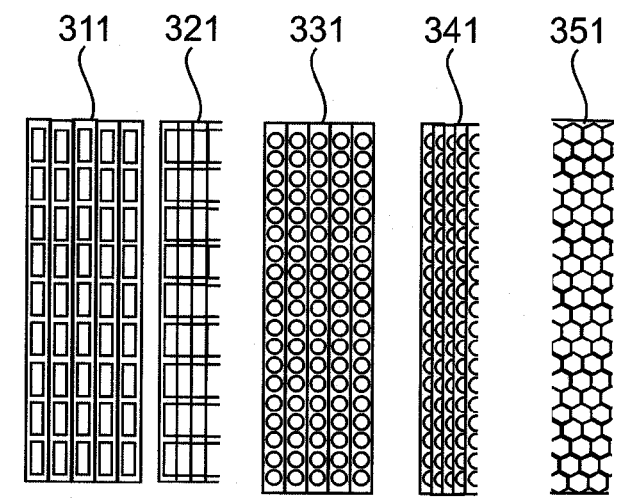
Figure 4:
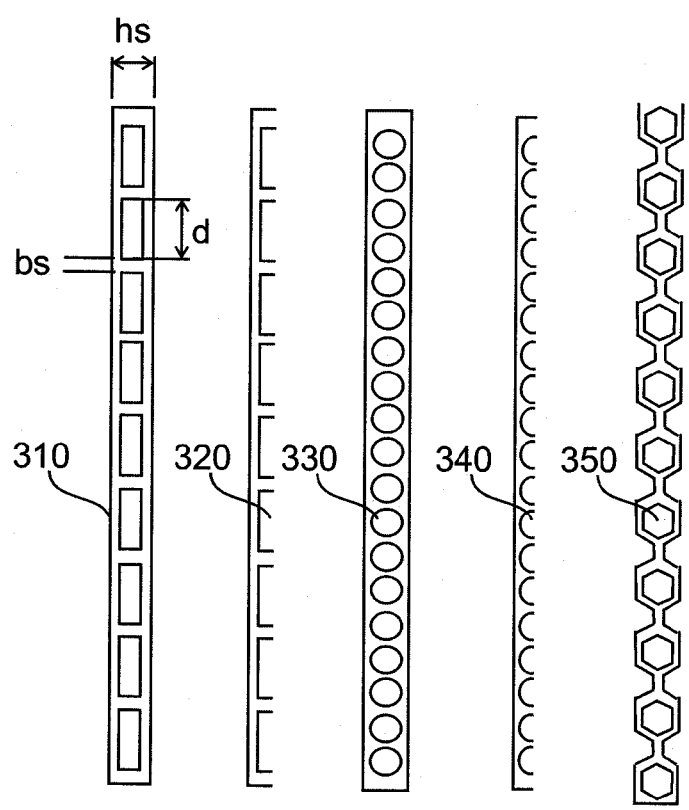

FIG. 4 Diagram of the construction of various plate stacks (cross section AA' from FIG. 3)

FIG. 5 Diagram of the application of the plastic bag 50 to a plate stack 1 (cross section AA' from FIG. 3)

Figure 7:
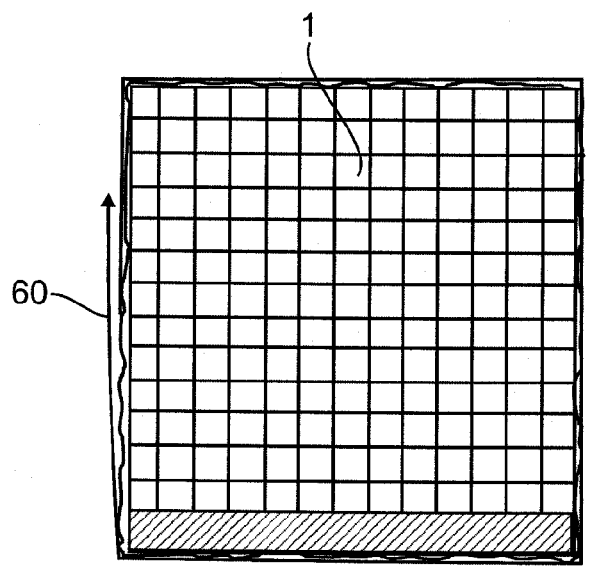

FIG. 6 and FIG. 7 Tightening and securing of the plastic bag 50 on a plate stack 1 (cross section)

Figure 8:
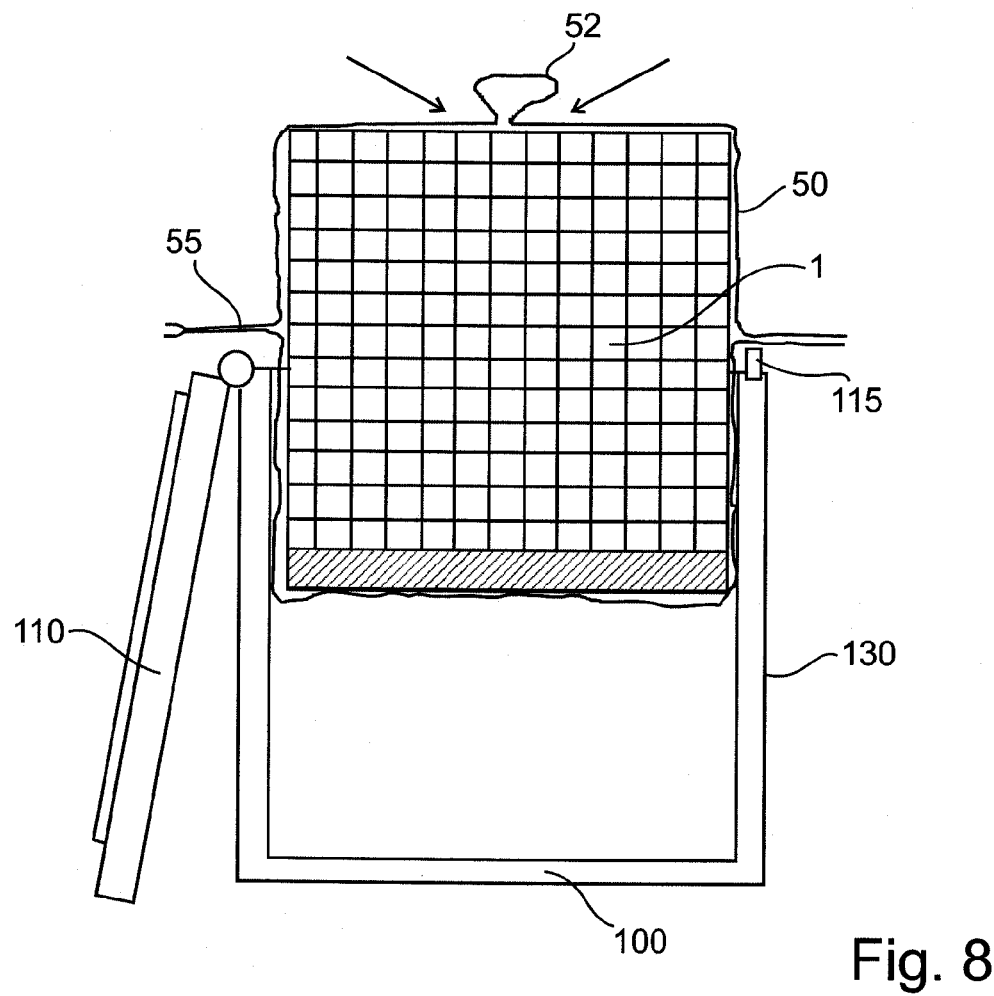
Figure 9:
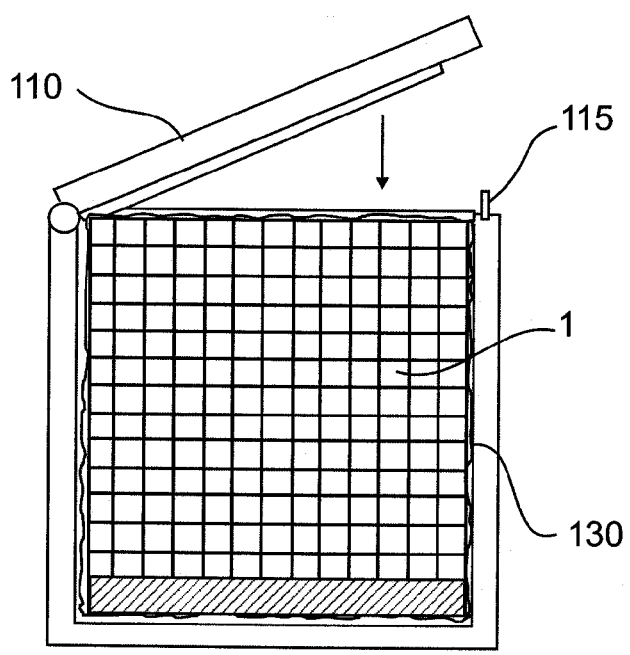

FIG. 8 and FIG. 9 Alternative tightening and securing of the plastic bag 50 on a plate stack 1 using framework 130 and lid 110 (cross section)

Figure 10:
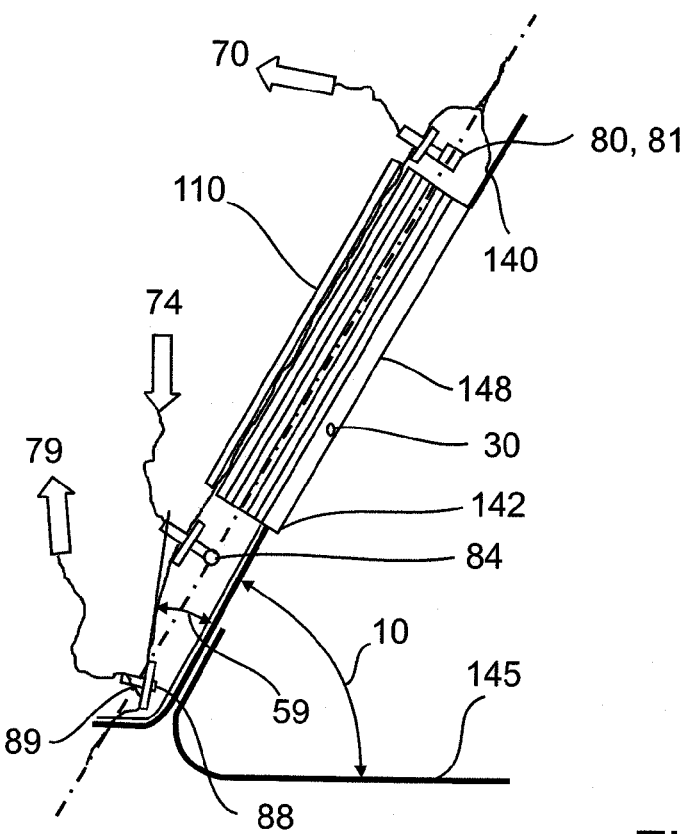

FIG. 10 Side views of the solids separators according to the invention containing plate stack 1 on frame 140.

FIG. 11 Front views of the solids separators according to the invention containing plate stack 1 on frame 140.

FIG. 12 Longitudinal sections of the solids separators according to the invention containing plate stack 1 on frame 140 with framework 130 and lid 110.

FIG. 13 Front views of the solids separators according to the invention containing plate stack 1 on their frame 140 with framework 130 and lid 110.

Figure 14:
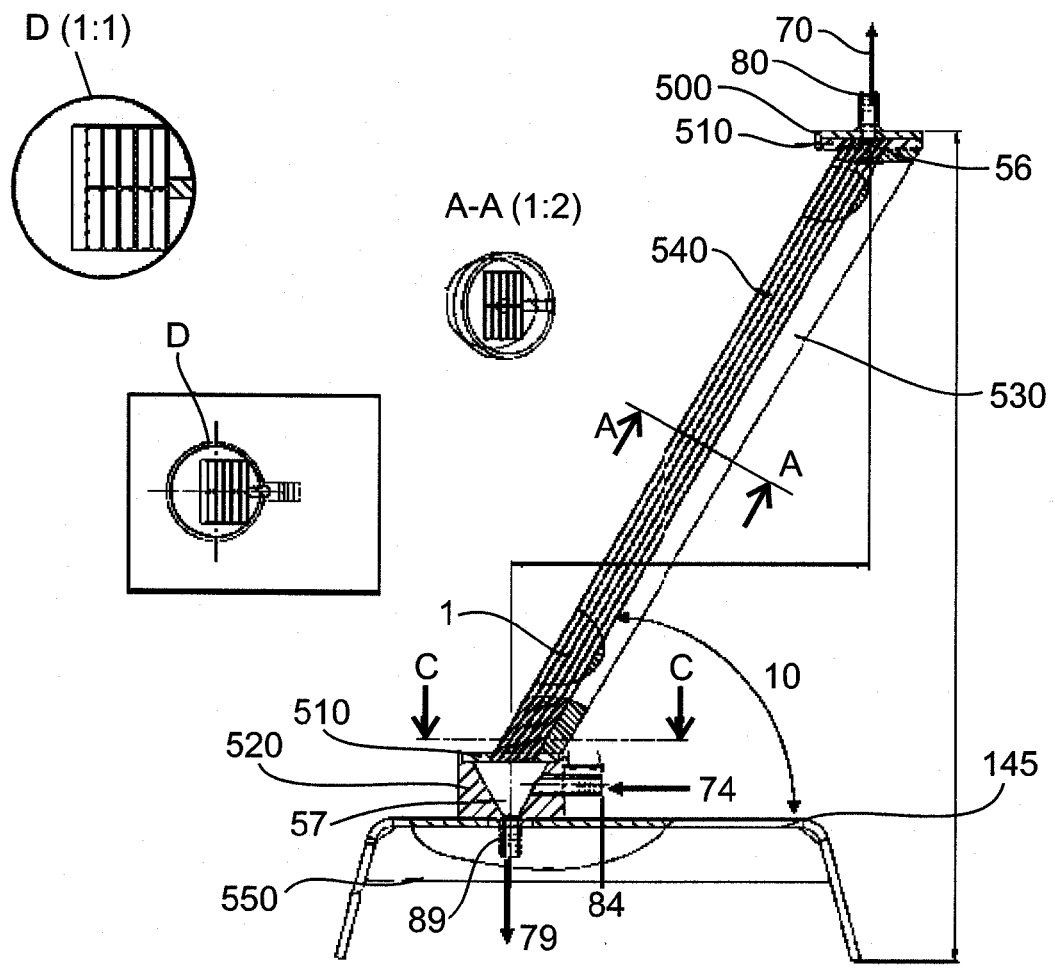
Figure 14:
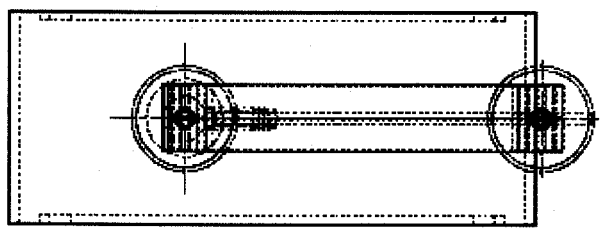

FIG. 14 Longitudinal section of the solids separator according to the invention on its console, view from above, cross sections (A-A, C-C) and enlargements (D).

Figure 15:
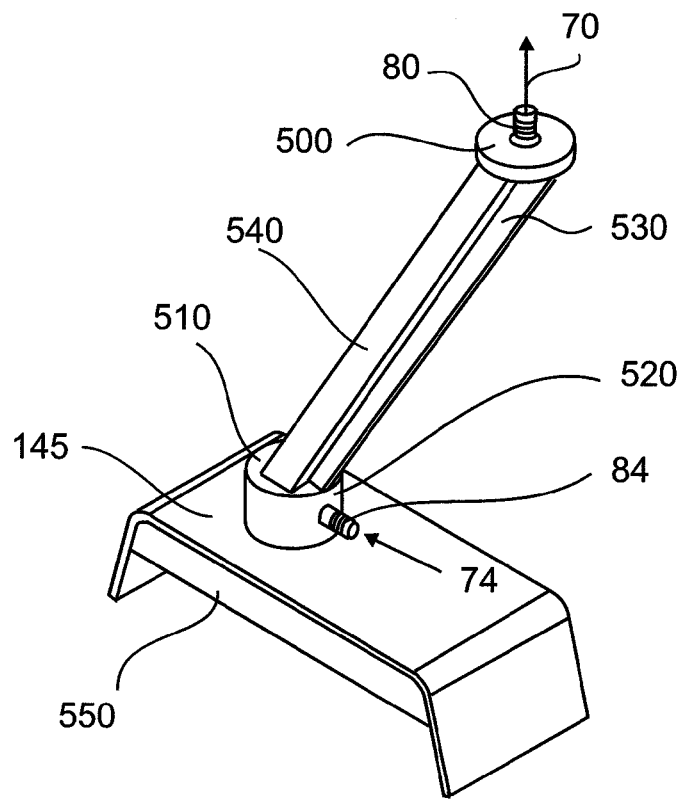

FIG. 15 Three-dimensional diagram showing the solids separators according to the invention on its console FIG. 16 Process diagram of a perfusion reactor. To reduce the respiratory activity of the cells in the bioreactor outlet, the temperature thereof is lowered to a lower level in a cooling device as quickly as possible after removal. This prevents the cells in the cell separator from staying too long in an oxygen-limited state, which could damage the cells physiologically. In the example shown, the separator 640 consists of a separation bag 620 and an integrated cooling device 600. The liquid flows between bioreactor 610 and separator 640 are adjusted by the low-shear pumps 630 and 631. Other interconnections, for example the positioning of one of the two pumps 630 and 631 in the bioreactor outlet, are also conceivable.

REFERENCE SIGNS

1 Plate stack/separator surface area
5 Strut width
8 Plate interval
10 Angle
13 Length
15 Width
18 Height
30 Supporting plate
50 Plastic bag
52 Excess/fold
55 Welding seam
56 Harvest stream collection region
57 Solids collection region
58 Angle
59 Angle
60 Fastening strap
70 Harvest stream (harvest)
74 Bioreactor mixture/feed
79 Recirculation
80 Feed-through
81 Flow inverter 84 Feed-through
85 Horizontal distributor
86 Inlet flow
88 Central suction port
89 Feed-through
90 Connection plate
100 Housing
110 Lid
112 Extension
115 Fastening element
130 Framework
140 Frame
142 Projection
145 Frame foot
148 Support
200 Vibrator
210 Assembly plate
Profiles of a Plate Stack
311 Plate stack
320 Rectangular profile
321 Plate stack
330 Round profile
331 Plate stack
340 Round profile
341 Plate stack
350 6-corner profile
351 Plate stack
500 Collector
510 Plug plates
520 Funnel
530 Stiffening bracket
540 Web-plate base body
550 Console
600 Cooling device
610 Bioreactor
620 Separation device
630, 631 Pumps
640 Separator=separation bag+cooling device possibly integrated in the frame or container.
650 Culture medium The studies which led to this invention were funded according to the grant agreement "Bio.NRW: MoBiDik—Modulare Bioproduktion—Disposable and Kontinuierlich" (Bio.NRW: MoBiDik—Modular bioproduction—Disposable and Continuous) (grant number w1004ht022a) as part of the European Regional Development Fund (ERDF).

The invention claimed is:

1. An inclined channel solids separator for retaining and recirculating solids from a reactor mixture, comprising the following elements:
    an upper region of the solids separator having one or more feed-throughs/fittings for removing a harvest stream separated from the cells (=harvest) from a harvest stream collection region connected to
    a separation region including channels formed by a plate stack comprising one or more single-layer or multilayer plastic web plates, which stack is tilted during operation at an angle of from 30° to 80° with respect to the horizontal, connected to
    a lower segment of the solids separator having one or more feed-throughs or fittings for flow distribution of the reactor mixture above
    a solids collection region which is downwardly tapered for collecting cells by means of gravity
    wherein the web plates are joined by adhesive bonding and/or fasteners,
    wherein the plate stack is formed from a profiled plate having a smooth side and a side having a succession of struts and grooves at constant intervals, and
    wherein the ratio of strut height to channel width hs/d is $0.01 \leq hs/d \leq 5$, with a restriction that the two dimensions hs and d are both greater than or equal to 3 mm.

2. The inclined channel solids separator of claim 1, wherein the solids collection region is downwardly tapered in a conical or pyramidical manner.

3. The inclined channel solids separator of claim 2 comprised in a gamma-sterilizable plastic bag through which flow passes, wherein the plastic bag comprises:
    the upper region, comprising the feed-throughs/fittings for removing the harvest stream separated from solids from the harvest stream collection region,
    an upper segment of a central region, comprising the separation region with the plate stack comprising one or more single-layer or multilayer plastic web plates,
    a lower segment of the central region, comprising the lower segment of the solids separator wherein the feed-throughs or fittings having horizontal distributors for uniform horizontal flow distribution of a cell culture solution via an infeed surface area, and
    a lower region, comprising the solids collection region, which is downwardly tapered in a conical manner for collecting the solids by means of gravity.

4. The inclined channel solids separator of claim 1, wherein the solids collection region has one or more feed-throughs or fittings for removing the solids.

5. The inclined channel solids separator of claim 4 comprised in a gamma-sterilizable plastic bag through which flow passes, wherein the plastic bag comprises:
    the upper region, comprising the feed-throughs/fittings for removing the harvest stream separated from solids from the harvest stream collection region,
    an upper segment of a central region, comprising the separation region with the plate stack comprising one or more single-layer or multilayer plastic web plates,
    a lower segment of the central region, comprising the lower segment of the solids separator wherein the feed-throughs or fittings having horizontal distributors for uniform horizontal flow distribution of a cell culture solution via an infeed surface area, and
    a lower region, comprising the solids collection region, which is downwardly tapered in a conical manner for collecting the solids by means of gravity.

6. The inclined channel solids separator of claim 1, which comprises at least one disposable sensor in the interior.

7. The inclined channel solids separator of claim 6 comprised in a gamma-sterilizable plastic bag through which flow passes, wherein the plastic bag comprises:
    the upper region, comprising the feed-throughs/fittings for removing the harvest stream separated from solids from the harvest stream collection region,
    an upper segment of a central region, comprising the separation region with the plate stack comprising one or more single-layer or multilayer plastic web plates,
    a lower segment of the central region, comprising the lower segment of the solids separator wherein the feed-throughs or fittings having horizontal distributors for uniform horizontal flow distribution of a cell culture solution via an infeed surface area, and
    a lower region, comprising the solids collection region, which is downwardly tapered in a conical manner for collecting the solids by means of gravity.

8. The inclined channel solids separator of claim 1, wherein the separation region comprises a multiplicity of channels arranged next to one another in the plate stack.

9. The inclined channel solids separator of claim 8 comprised in a gamma-sterilizable plastic bag through which flow passes, wherein the plastic bag comprises:
the upper region, comprising the feed-throughs/fittings for removing the harvest stream separated from solids from the harvest stream collection region,
an upper segment of a central region, comprising the separation region with the plate stack comprising one or more single-layer or multilayer plastic web plates,
a lower segment of the central region, comprising the lower segment of the solids separator wherein the feed-throughs or fittings having horizontal distributors for uniform horizontal flow distribution of a cell culture solution via an infeed surface area, and
a lower region, comprising the solids collection region, which is downwardly tapered in a conical manner for collecting the solids by means of gravity.

10. The inclined channel solids separator of claim 1, wherein:
the separation region formed by the plate stack composed of single-layer or multilayer plastic web plates forms a web-plate base body, which is plugged into plug plates at a top and bottom,
the lower segment and the solids collection region, which is downwardly tapered in a conical manner, is a funnel, and
all the elements of the solids separator comprise plastic.

11. The inclined channel solids separator of claim 1 comprised in a gamma-sterilizable plastic bag through which flow passes, wherein the plastic bag comprises:
the upper region, comprising the feed-throughs/fittings for removing the harvest stream separated from solids from the harvest stream collection region,
an upper segment of a central region, comprising the separation region with the plate stack comprising one or more single-layer or multilayer plastic web plates,
a lower segment of the central region, comprising the lower segment of the solids separator wherein the feed-throughs or fittings having horizontal distributors for uniform horizontal flow distribution of a cell culture solution via an infeed surface area, and
a lower region, comprising the solids collection region, which is downwardly tapered in a conical manner for collecting the solids by means of gravity.

12. A bioreactor unit comprising a bioreactor connected to the inclined channel solids separator of claim 1.

13. An inclined channel solids separator for retaining and recirculating solids from a reactor mixture, comprising the following elements:
an upper region of the solids separator having one or more feed-throughs/fittings for removing a harvest stream separated from the cells (=harvest) from a harvest stream collection region connected to
a separation region including channels formed by a plate stack comprising one or more single-layer or multilayer plastic web plates, which stack is tilted during operation at an angle of from 30° to 80° with respect to the horizontal, connected to
a lower segment of the solids separator having one or more feed-throughs or fittings for flow distribution of the reactor mixture above
a solids collection region which is downwardly tapered for collecting cells by means of gravity
wherein the web plates are joined by adhesive bonding and/or fasteners,
wherein the inclined channel solids separator is comprised in a gamma-sterilizable plastic bag through which flow passes, wherein the plastic bag comprises:
the upper region, comprising the feed-throughs/fittings for removing the harvest stream separated from solids from the harvest stream collection region,
an upper segment of a central region, comprising the separation region with the plate stack comprising one or more single-layer or multilayer plastic web plates,
a lower segment of the central region, comprising the lower segment of the solids separator wherein the feed-throughs or fittings having horizontal distributors for uniform horizontal flow distribution of a cell culture solution via an infeed surface area, and
a lower region, comprising the solids collection region, which is downwardly tapered in a conical manner for collecting the solids by means of gravity.

14. The inclined channel solids separator of claim 13, wherein the channels have a channel length L of from 30% to 95% of a length LK of the plastic bag.

15. The inclined channel solids separator of claim 13, further comprises a container for accommodating the solids separator,
wherein the container has at least one interior for accommodating the solids separator,
wherein said interior comprises walls matched to a shape of the solids separator by means of the shape of the solids separator, walls enclose the interior and demarcate said interior from an outside world, an opening for introducing the solids separator from above into the container.

* * * * *